United States Patent
Haist et al.

(10) Patent No.: US 10,877,647 B2
(45) Date of Patent: Dec. 29, 2020

(54) ESTIMATIONS WITHIN DISPLAYS

(71) Applicant: Hewlett-Packard Development Company, L.P., Spring, TX (US)

(72) Inventors: Brandon James Lee Haist, Houston, TX (US); Alexander Wayne Clark, Spring, TX (US); Ricky Thomas Burks, Houston, TX (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 16/476,023

(22) PCT Filed: Mar. 21, 2017

(86) PCT No.: PCT/US2017/023315
§ 371 (c)(1),
(2) Date: Jul. 3, 2019

(87) PCT Pub. No.: WO2018/174854
PCT Pub. Date: Sep. 27, 2018

(65) Prior Publication Data
US 2019/0377477 A1  Dec. 12, 2019

(51) Int. Cl.
*G06F 3/01* (2006.01)
*G06F 3/0484* (2013.01)
(Continued)

(52) U.S. Cl.
CPC .......... *G06F 3/04842* (2013.01); *G06F 3/013* (2013.01); *G06F 3/015* (2013.01);
(Continued)

(58) Field of Classification Search
None
See application file for complete search history.

(56) References Cited

U.S. PATENT DOCUMENTS

2006/0061544 A1  3/2006 Min
2006/0238707 A1  10/2006 Elvesjo et al.
(Continued)

FOREIGN PATENT DOCUMENTS

| KR | 20150104781 | 9/2015 |
| WO | WO 2016139576 | 9/2016 |

OTHER PUBLICATIONS

Machine translation of KR 101272811 B1 into English. (Year: 2013).*
(Continued)

*Primary Examiner* — Brian M Butcher
(74) *Attorney, Agent, or Firm* — Brooks Cameron & Huebsch PLLC (US LC)-USD (57) ABSTRACT

Example implementations relate to virtual reality/augmented reality signals. For example, a non-transitory computer readable medium storing instructions executable by a processing resource to receive eye-tracking signals from a camera mounted on a display. The instructions can cause the processing resource to estimate a location on a display using the eye-tracking signals. The instructions can cause the processing resource to receive electroencephalographic (EEG) signals. The instructions can cause the processing resource to confirm the estimated location based on the eye-tracking signals and the EEG signals.

15 Claims, 5 Drawing Sheets

(51) Int. Cl.
*G06F 3/023* (2006.01)
*G06F 3/0354* (2013.01)

(52) U.S. Cl.
CPC .............. *G06F 3/017* (2013.01); *G06F 3/023* (2013.01); *G06F 3/03543* (2013.01); *G06F 2203/011* (2013.01)

(56) References Cited

U.S. PATENT DOCUMENTS

| | | |
|---|---|---|
| 2007/0255127 A1 | 11/2007 | Mintz |
| 2014/0009390 A1 | 1/2014 | Bjorklund et al. |
| 2014/0347265 A1* | 11/2014 | Aimone ................ A61M 21/00 345/156 |
| 2014/0354534 A1 | 12/2014 | Mullins |
| 2014/0368442 A1 | 12/2014 | Vahtola |
| 2015/0073907 A1* | 3/2015 | Purves ................ G06Q 20/384 705/14.58 |
| 2016/0187976 A1 | 6/2016 | Levesque |
| 2016/0246384 A1 | 8/2016 | Mullins |
| 2016/0259977 A1* | 9/2016 | Asbun ................ A61B 5/1112 |
| 2018/0049636 A1* | 2/2018 | Miller ................ A61B 5/0476 |
| 2018/0081430 A1* | 3/2018 | Konz ................ G06F 3/015 |
| 2018/0107274 A1* | 4/2018 | Li ................ G02B 27/0172 |
| 2018/0188807 A1* | 7/2018 | Cimenser ............. A61B 5/6803 |
| 2018/0196511 A1* | 7/2018 | Chae ................ G06F 3/011 |
| 2019/0307350 A1* | 10/2019 | Sridhar ................ A61B 5/6803 |

OTHER PUBLICATIONS

Machine translation of KR 20120060978 A into English. (Year: 2012).*

Craig, E.; Mindmaze: A VR Interface From the Future ;Feb. 14, 2016; 1a,1b,1,3a,3b,6; https://www.digitalbodies.net/virtual-reality/mindmaze-a-vr-interface-from-the-future.

* cited by examiner

ESTIMATIONS WITHIN DISPLAYS

BACKGROUND

Headsets may be used in virtual reality (VR) and/or augmented reality (AR) systems. VR and/or AR headsets may be worn by a user and may include displays to provide a "virtual" and/or "augmented" reality to the user by providing images, screens, and/or other visual stimuli to the user via the displays.

DETAILED DESCRIPTION

Head mounted displays may be used in virtual reality (VR) and/or augmented reality (AR) systems. In some examples, a VR system may cover a user's eyes and provide visual stimuli to the user via a display, thereby substituting a "virtual" reality for actual reality. The VR system may allow the user to interact with the "virtual" reality world through games, educational activities, group activities, and the like.

An AR system may provide an overlay transparent or semi-transparent screen in front of and facing toward a user's eyes such that reality is "augmented" with additional information such as graphical representations and/or supplemental data. For example, an AR system may overlay transparent or semi-transparent weather information, directions, and/or other information on an AR display for a user to examine.

VR/AR headsets may be used in many different fields and/or for many different applications. For example, VR/AR headsets may be used in gaming, aviation, engineering, medicine, geopositioning, training, military, government (e.g., fire, police, etc.), and sports, among other fields.

An example of a VR/AR device may include a display and a strap and/or head portion coupled to a display screen. The display can include a housing that includes a display screen (e.g., an LCD display screen). The strap may facilitate keeping the display in a specific position on a user's head such that the user is able to see the visual stimuli on the display. In some example, a head portion can be like a cap on a user's head that holds the display in place. The display can include cameras and/or sensors. The sensors can receive signals (e.g., sensory inputs) that indicate eye movement. The eye movement can include pupil movement indicating a change in what the user is looking at and/or a change in gaze of the user. The sensors to monitor eye movement can receive signals that indicate a gaze of a user's eyes. The gaze of the user's eyes can indicate a location on an image displayed in the display that the user would like to select.

However, errors in detecting eye gaze acid/or errors in detecting what the user would like to select can lead to selection of items in the VR system that the user does not wish to select.

The strap and/or display can include sensors. For example, the strap and/or display sensors can include an electroencephalographic (EEG) sensor. In some examples, the EEG signals can include excitation signals sent by the brain of the user and received by the EEG sensors. The excitation signals, in correlation with the eye movement monitoring, can confirm that selection of a particular item is correct. For example, a user's gaze can indicate that the user would like to select a particular item in the VR/AR system. An EEG signal can confirm that the user did want to select that particular item. While EEG signals are used, in this example, to indicate confirmation, examples are not so limited. For example, any number of additional sensor signals can confirm that the user did select a particular item. The additional sensor signals can include voice, gesture, etc. that are in addition to the eye tracking monitoring. In addition, other sensor signals can indicate that the user wants to select the particular item. The other sensor signals can include input by the user through a mouse, a keyboard, handset, controller, voice activation, etc.

Examples of the disclosure include apparatuses, systems, and methods for virtual reality/augmented reality signals. In some examples, an apparatus may include a display with sensors and a strap including sensors. In some examples, the apparatus may include infrared (IR) cameras in the display. In some examples, the apparatus may include EEG sensory probes on the strap.

Figure 1:
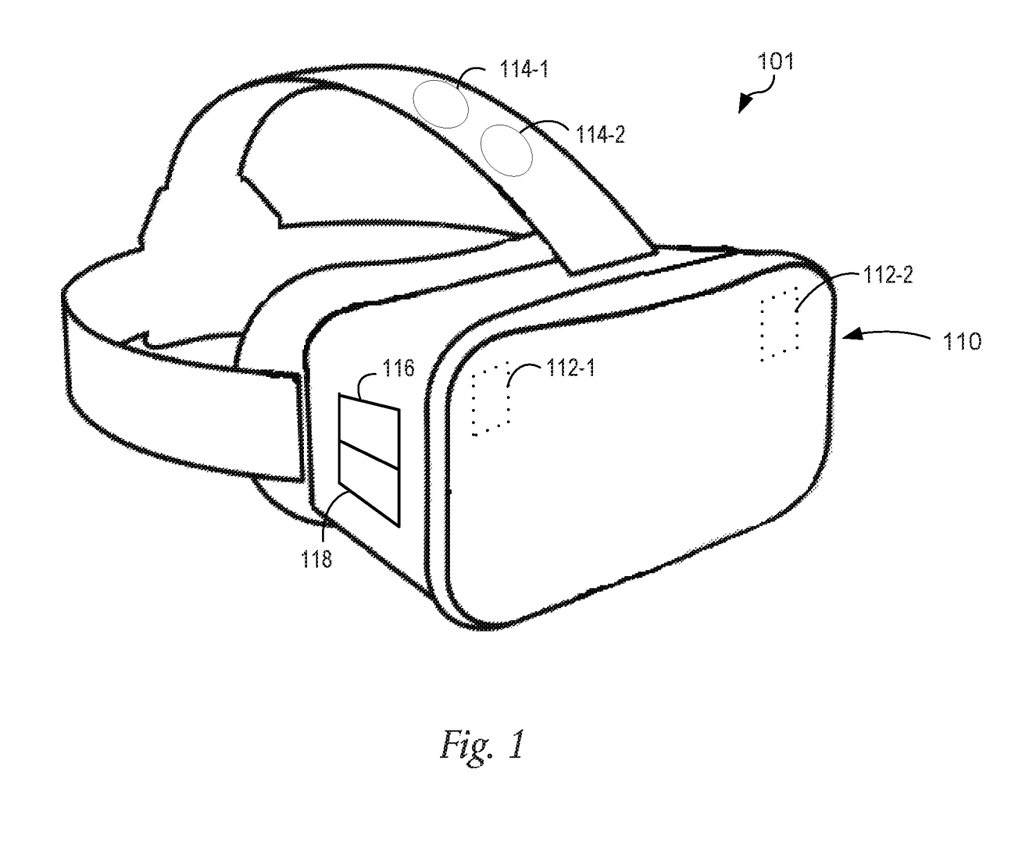
FIG. 1 illustrates an example of an apparatus for estimations within displays consistent with the disclosure.

FIG. 1 illustrates an example of an apparatus 101 for estimations within displays consistent with the disclosure. As illustrated in FIG. 1, the apparatus 101 can include a display 110. The display 110 can include a portion shaped like goggles that includes a display screen. The display 110 can include cameras 112-1, 112-2. The cameras 112-1, 112-2 can be infrared (IR) cameras used to detect eye movement of a user wearing the apparatus 101. The cameras 112-1, 112-2 can be mounted in the display a particular distance from the user to facilitate monitoring of a gaze of the user's eyes.

The apparatus 101 can include sensors 114-1, 114-2 to contact a head of the user. The sensors 114-1, 114-2 can include EEG sensors that receive EEG signals. The sensors 114-1, 114-2 can be in contact with a front portion of the user's head. The EEG sensors can be EEG probes used to detect EEG signals and/or readings from a brain of the user. EEG readings can refer to electrophysiological monitoring of electrical activity of the brain. The EEG sensors can be positioned along a scalp of the user. EEG measures voltage fluctuations resulting from ionic current within neurons of the brain. Applications of EEG can focus on spectral content of EEG, such as a type of neural oscillation (sometimes referred to as "brain waves") that can be observed in EEG signals.

The EEG signals can indicate an excitation signal from the user that may indicate that the user has viewed something the user is interested in. For example, an excitation signal of the user can be correlated with a focus of a gaze of a user's eye, such that the eye is focused on something the user would like to select and the excitation signal is confirming that selection.

The apparatus 101 can include a processing resource 116 and a memory resource 118 that is embedded within the display 110 of the apparatus 101. However, examples are not so limited. The processing resource 116 and the memory resource 118 may be located in any number of different locations. For example, the processing resource 116 and the memory resource 118 may be located on the strap and/or head portion of the apparatus 101. The processing resource 116 and the memory resource 118 may be located on an external processing device such as a computer that the apparatus 101 is coupled to. The processing resource 116 and the memory resource 118 can be used in conjunction with collecting eye movement tracking signals and/or other sensory signals to determine item to select, as will be described further in association with FIGS. 3-5.

Figure 2:
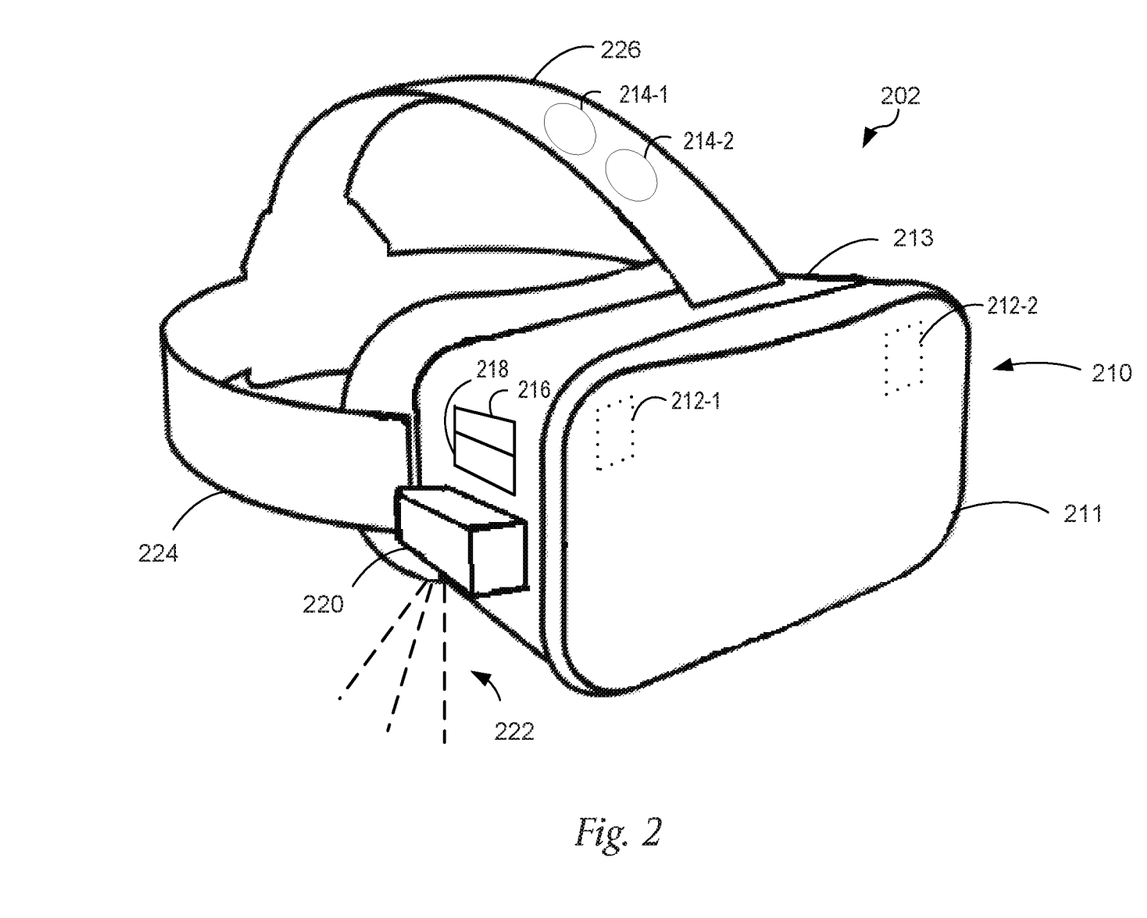
FIG. 2 illustrates an example of an apparatus for estimations within displays consistent with the disclosure.

FIG. 2 illustrates an example of an apparatus 101 for estimations within displays consistent with the disclosure. As illustrated in FIG. 2, the apparatus 202 can include a display 210. The display 210 can include a housing 213 and a display screen 211. The display 210 can include cameras 212-1, 212-2. The cameras 212-1, 212-2 can be infrared (IR) cameras used to detect eye movement of a user wearing the apparatus 202. The cameras 212-1, 212-2 can be mounted in the display a particular distance from the user to facilitate monitoring of a gaze of the user's eyes. That is, in some examples, the cameras 212-1, 212-2 can be mounted in a top of the housing 213 of the display 210 and in front of the display screen 211.

The apparatus 202 can include sensors 214-1, 214-2 located on an upper head portion 226 (e.g., an upper strap) for contact with a head of the user. The apparatus 202 can include a lower head portion 224 (e.g., a lower strap). The sensors 214-1, 214-2 can include EEG sensors. The sensors 214-1, 214-2 can be in contact with a front portion of the user's head. The EEG sensors can be EEG probes used to detect EEG readings from a brain of the user.

The EEG signals can indicate an excitation signal from the user that may indicate that the user has viewed something the user is interested in. For example, an excitation signal of the user can be correlated with a focus of a gaze of a user's eye, such that the eye is focused on something the user would like to select and the excitation signal is confirming that selection.

The apparatus 202 can include a processing resource 216 and a memory resource 216 that is embedded within the display 210 of the apparatus 202. The processing resource 216 and the memory resource 118 can be used in conjunction with collecting eye movement tracking signals and/or other sensory signals to determine an item to select, as will be described further in association with FIGS. 3-5. For example, the processing resource 216 and the memory resource 218 can be used to collect additional signals including a selection from a mouse, a keyboard, handset controller, gesture, etc.

The display 210 of the apparatus 202 can include a camera 220. The camera 220 can be an IR camera mounted to the side of the display 210. The camera 320 can be facing downward and can be viewing movement below the camera, indicated by dotted lines 222. The camera 220 can be used to detect movements, such as gesture movements, of a user to determine additional confirmation sensory signals. For example, in response to eye movement indicating an item to select made by a user, EEG signals along with gesture movements can be used to confirm the item selection. An EEG signal including an excitation signal can indicate that the user tended to select the item. Gesture movements below the camera 220 can include are arm and/or hand moving and/or pointing toward a direction of what the user is viewing can indicate that the user wants to interact with what is being displayed in the display 210. These gesture movements can indicate, along with the eye tracking and the EEG excitation signal, that the user is intending to select the item.

Figure 3:
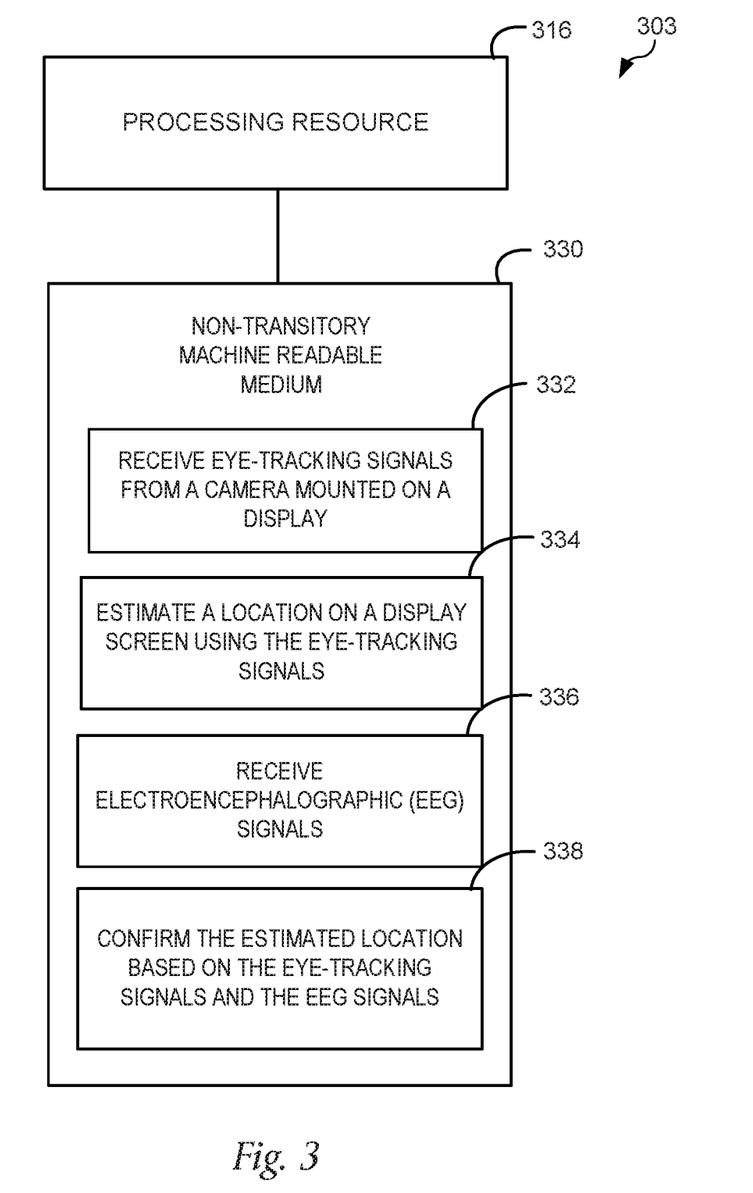
FIG. 3 illustrates a diagram of an example of a non-transitory computer readable medium and processing resource for estimations within displays consistent with the disclosure.

FIG. 3 illustrates a diagram 303 of an example of a non-transitory computer readable medium 330 and processing resource 316 for estimations within displays consistent with the disclosure. In some examples, the processing resource(s) 316 may process and/or control data received from inputs of an apparatus (e.g., apparatus 101 and 202 in FIGS. 1 and 2, respectively). A memory resource can be used to store instructions executed by the processing resource 316 to perform operations as described herein. A processing resource 316 may execute instructions stored on the non-transitory machine readable medium 330. The non-transitory machine readable medium 330 may be any type of volatile or non-volatile memory or storage, such as random access memory (RAM), flash memory, read-only memory (ROM), storage volumes, a hard disk, or a combination thereof.

The example medium 330 may store instructions 332 executable by a processing resource 316 to receive eye-tracking signals from a camera (e.g., cameras 112-1, 112-2 in FIG. 1) mounted on a display (such as a display 110 illustrated in FIG. 1). The eye-tracking signals can include movement of eyes of a user. The eye-tracking signals can indicate movement of pupils of a user captured by the camera. The movement of the eyes can indicate that a user is gazing at different items displayed in a virtual reality (VR)/augmented reality (AR) system. Movement of the eyes can indicate that the user is looking for items to select but has not rested on a particular item to select. Cessation of movement of the eyes can indicate that the user may have stopped at a particular item to select and wants to select that item. A gaze at the particular item for a period of time can indicate that the user would like to select the item. The period of time can be an extended period of time and/or a period of time that reaches a particular threshold of time. For example, 3 seconds may be indicated as a threshold of time for a user to gaze at an item to indicate that the user wants to select the item. However, any period of time can be used as a threshold time period. In addition, previously designated gaze behavior can be used to indicate a selection of an item. For example, an eye gaze that is changing and suddenly stops to rest on a gaze at a particular item.

The example medium 330 may store instruction executable by a processing resource 316 to analyze the received eye-tracking signals to estimate a location on a display screen. The estimated location can be an estimate of where on the display screen the user is looking. The location can correlate to a particular item and/or button within the VR/AR experience that may select and/or choose something to manipulate in the experience, such as a menu selection, a decisions selection, etc. The received eye-tracking signals can be analyzed to determine particular patterns in movement of the eyes. The analysis can be based on previous eye movement of the user. For example, previous eye movement may have indicated an item to select in an image and the VR/AR system may have selected that item. In response to the user indicating the selection was correct, the eye movements may be recorded as indicating selection. In response to the user indicating that the selection was incorrect, the eye movements may be recorded as eye movements that indicate a false positive or a false selection. In this way, behavior of a user, in this example eye movement of the user, can be learned and used for later determination of what the user may want to do in the AR/VR environments.

The example medium 330 may store instructions executable by a processing resource 316 to analyze the received eye-tracking signals based on analysis of previously received eye-tracking signals and an estimation success of the respective analysis. That is, the estimation success can be an amount of success that respective estimations achieved in choosing the location. As each estimation is confirmed as successful by a user, an estimation success rate can increase and a confidence level of particular eye movements correlating to successful estimations can increase. The estimation success rate can be a percentage of success for a particular eye movement detected. The estimation success rate can be an indication by a user of how successful the selection was on a numbering scale, etc.

The example medium 330 may store instructions 334 executable by a processing resource 316 to estimate a location on a display screen using the eye-tracking signals. The display screen can display an image in a VR/AR system. The image can be a whole image that is separate from a reality surrounding the user, such as in virtual reality where the surrounding reality is not used in the virtual reality world. In contrast, the image can include a superimposed image over the surrounding reality such that the surrounding reality is used as a backdrop to the image. In this way, the image augments the surrounding reality and/or adds to that reality. The estimated location can be a location on the display screen that correlates to the image of either the VR or AR environments. The estimated location can be determined based on the previously mentioned threshold period of time that a gaze of the user may occur.

The example medium 330 may store instructions 336 executable by a processing resource 316 to receive EEG signals. The EEG signals (received from sensors 114-1, 114-2 in FIG. 1 and 214-1, 214-2 in FIG. 2) can be received from EEG probes positioned on a head of a user. The EEG signals can indicate brain activity that indicates whether a user selected a location on the display screen.

The example medium 330 may store instructions 338 executable by a processing resource 316 to confirm the estimated location based on the eye-tracking signals and the EEG signals. The confirmation can include detecting an excitation response in the EEG signals that corresponds to the eye-tracking signals. The confirmation may be based on a particular threshold amount of excitation in the excitation response. For example, a brain wave may reach a excitation level that indicates that a threshold excitation has been reached. In response to the excitation level being reached, the selection of the item may be confirmed. In response to the excitation level not being reached, the selection of the item may be unconfirmed and/or confirmed as in error.

Figure 4:
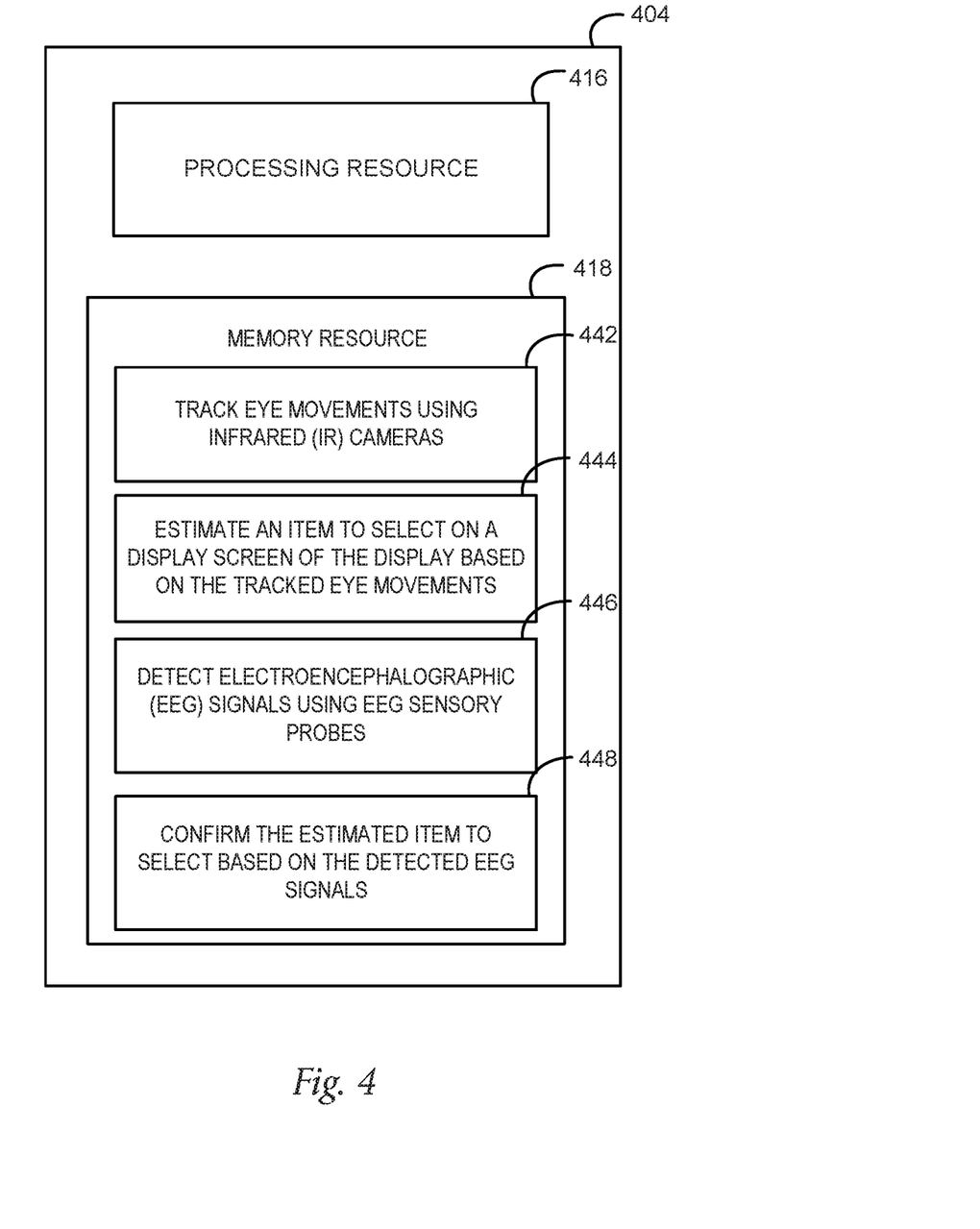
FIG. 4 illustrates a diagram of an example of a processing resource and memory resource for estimations within displays consistent with the disclosure.

FIG. 4 illustrates a diagram of an example of an apparatus 404 for estimations within displays consistent with the disclosure. The apparatus 404 can include a processing resource 416 and a memory resource 418. The processing resource 416 may execute instructions stored in the memory resource 418. By way of example, the memory resource 418 may be any type of volatile and/or non-volatile memory or storage, such as random access memory (RAM), flash memory, read-only memory (ROM), storage volumes, a hard disk, or a combination thereof. The memory resource 418 can be used to store data and/or instructions. The memory resource may store machine readable instructions 442, 444, 446, 448 that, when executed by the processing resource 416, cause the processing resource 416 to perform a particular operation.

The memory resource 418 may store instructions 442 executable by a processing resource 416 to track eye movements using an IR camera (such as cameras 112-1, 112-2 in FIG. 1 and cameras 212-1, 212-2 in FIG. 2). The camera can include more than one IR cameras. The number of IR cameras can include two IR cameras positioned in front of eyes of a user. The IR cameras can be positioned a particular distance from eyes of a user to monitor a gaze of the eyes and/or a change in the gaze.

The memory resource 418 may store instructions 444 executable by a processing resource 416 to estimate an item to select on a display screen of a display based on the tracked eye movements. Selection of the estimated item can be delayed until further confirmation that the item was intended to be selected is performed. The item can be estimated as selected by the user in response to a gaze of the user resting and/or stopping on the estimated item.

The memory resource 418 may store instructions 446 executable by a processing resource 416 to detect EEG signals using the EEG sensory probes. The EEG signals can include brain wave activity of a brain of the user. The EEG signals can include graphs an or charts of electrical activity that indicate brain activity of the user. The electrical activity can include peaks and/or valleys of electrical activity. Excitation signals can be indicated by a peak in the electrical activity. Excitation signals can be indicated by a particular waveform of electrical activity detected in the brain.

The memory resource 418 may store instructions 448 executable by a processing resource 416 to confirm the estimated item to select based on the detected EEG signals. The confirmation of the estimated item can be determined by correlating an excitation signal with eye tracking movements. The correlation can include correlating a time that the excitation signal occurred and a time that the eye tracking movements exhibited particular behavior. For example, a peak in electrical activity may have occurred at the same time that eye movement stopped to gaze at a particular item. The particular item would have been estimated as an item to be selected and the EEG excitation of the peak can confirm that the item should be selected. While this is given as an example, examples are not so limited. Any number of correlations, such as peaks with previous successful selections indicating that a particular EEG activity indicates a current successful selection, may be performed.

The memory resource 418 may store instructions executable by the processing resource 416 to detect gesture movement of a user, where the machine readable instructions cause the processing resource to detect gestures from a user. The memory resource may store instructions executable by the processing resource 416 to confirm the estimated item based on the detected gestures. The estimated item may be confirmed by both the detected gestures and the EEG signals. In some examples, the EEG signals alone may not be sufficient to indicate confirmation but the added gesture movements may allow indication of confirmation. As an example, the EEG signals may not have reached a threshold excitation level but could be close to a threshold level. The gesture movements may provide enough data to indicate that the EEG signals on top of the gesture movements indicate confirmation.

Figure 5:
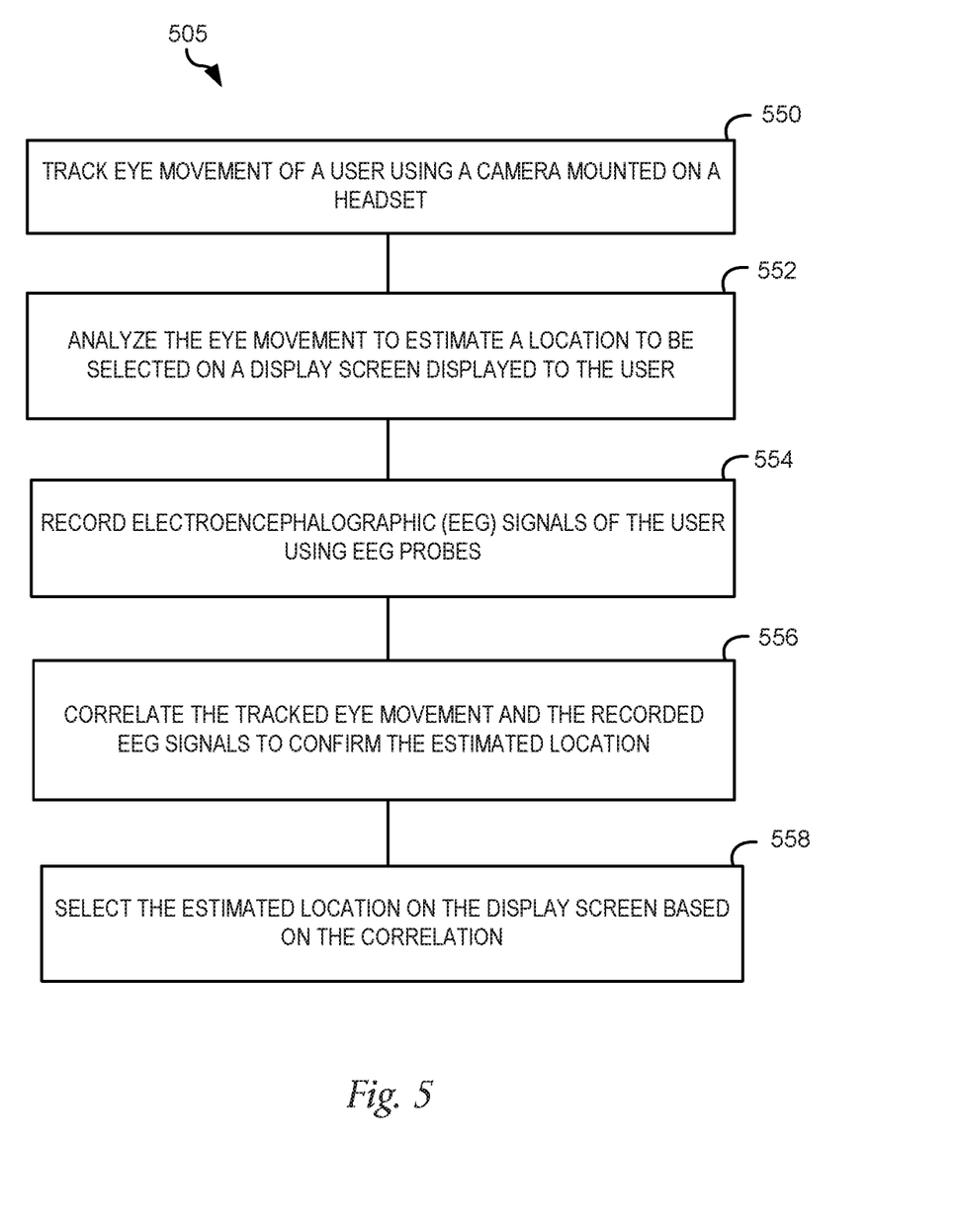
FIG. 5 illustrates a flow diagram for an example of a method for estimations within displays consistent with the disclosure.

FIG. 5 illustrates a flow diagram for an example of a method 505 for estimations within displays consistent with the disclosure. At 550, the method 505 includes tracking eye movement of a user using a camera mounted on a display. The camera can be mounted on a display. The camera can be mounted a particular distance from the eyes of the user to allow for monitoring of the eyes. A gaze of the eyes can be monitored in order to determine where on an image the eyes are gazing.

At 552, the method 505 can include analyzing the eye movement to estimate a location to be selected on a display screen displayed to the user. The eye movement can be analyzed to determine where the eyes are gazing. Based on the gaze of the eyes, a location on a display screen that the eyes are gazing at can be determined. The location on the display screen can be indicated as an estimate of where the user would like to select. Prior to selecting the location on the image, a confirmation (e.g., a verification) that the user intended to select that location can be performed.

At 554, the method 505 can include recording EEG signals of the user using EEG probes. The EEG probes can be placed on a front portion of the head of the user to detect signals from the front portion of the brain of the user. The EEG probes can detect particular electrical activity of the brain.

At 556, the method 505 can include correlating the tracked eye movement and the recorded EEG signals to confirm the estimated location. For example, the tracked eye movement can indicate a location on the image at a particular point in time. An EEG signals recorded at the particular point in time can be correlated with the tracked eye movement at the particular point in time, indicating that the user intended to select the location at the particular point in time. Tracked eye movement and EEG sensory signals can be correlated within a particular window of time, such as a range of 5 seconds, 10 seconds, etc. That is, the EEG signals may be delayed from the moment that the location was gazed at by the eyes. Further, the EEG signals may be delayed in providing an indication that the location and/or item estimated to select is the correct one.

At 558, the method 505 can include selecting the estimated location on the display screen based on the correlation. That is, the estimated location can be determined to be the correct location to select and the system can select that location. The estimated location of the display screen can include a button, a selection item, a character selection, etc. that the user would like to select. Subsequent to confirmation that the estimated location is the correct location to select, the estimated location can be selected.

In some examples, the method 505 includes selectin the estimated location by selecting a menu item in a virtual reality or augmented reality system. That is, the location can be a location of a menu item to be selected. The location can be an image of a character to be selected, etc. In some examples the method 505 can include detecting an input from a user indicating the location to be selected, wherein the input comprises selection on a keyboard, a mouse, a handset, a controller, speech of the user, a gesture, or a combination thereof. The speech of the user can be recorded using a microphone mounted to the display. The input can be correlated with the eye movement and the EEG signals to provide greater confidence in the estimated location.

In some examples, the method 505 includes detecting a gesture from the user indicating the location to be selected. The gesture can include hand movement, finger movement, leg movement, etc. The method 505 can include correlating the gesture with the tracked eye movement and the recorded EEG signals to confirm the estimated location. In some examples, when the tracked eye movement and the recorded EEG signals do not correlate, an indication that the estimated location is not confirmed can be provided.

In the foregoing detailed description of the present disclosure, reference is made to the accompanying drawings that form a part hereof, and in which is shown by way of illustration how examples of the disclosure may be practiced. These examples are described in sufficient detail to enable those of ordinary skill in the art to practice the examples of this disclosure, and it is to be understood that other examples may be utilized and that process, electrical, and/or structural changes may be made without departing from the scope of the present disclosure.

What is claimed:

1. A non-transitory computer readable medium storing instructions executable by a processing resource to:
   receive eye-tracking signals from a camera mounted on a display;
   estimate a location on a display screen using the eye-tracking signals;
   receive electroencephalographic (EEG) signals; and
   confirm the estimated location based on the eye-tracking signals and the EEG signals.

2. The medium of claim 1, further comprising instructions executable by the processing resource to estimate the location based on analysis of previously received eye-tracking signals.

3. The medium of claim 2, further comprising instructions executable by the processing resource to estimate the location based on:
   the analysis of the previously received eye-tracking signals; and
   an estimation success of the analysis of the previously received eye-tracking signals.

4. The medium of claim 1, wherein the eye-tracking signals a movement of pupils of a user captured by the camera.

5. The medium of claim 1, further comprising instructions executable by the processing resource to confirm the estimated location in response to detection of an excitation response in the EEG signals that corresponds to the eye-tracking signals.

6. A method, comprising:
   tracking eye movement of a user using a camera mounted on a display;
   analyzing the eye movement to estimate a location to be selected on a display screen displayed to the user;
   recording electroencephalographic (EEG) signals of the user using EEG probes;
   correlating the tracked eye movement and the recorded EEG signals to confirm the estimated location; and
   selecting the estimated location on the display screen based on the correlation.

7. The method of claim 6, wherein selecting the estimated location comprises selecting a menu item in a virtual reality system.

8. The method of claim 6, comprising detecting an input from a user indicating the location to be selected, wherein the input comprises a keyboard input, a mouse input, a handset input, a controller input, a gesture, and combinations thereof.

9. The method of claim 6, comprising:
   detecting a gesture from the user indicating the location to be selected; and
   correlating the gesture with the tracked eye movement and the recorded EEG signals to confirm the estimated location.

10. The method of claim 6, wherein, when the tracked eye movement and the recorded EEG signals do not correlate, indicating that the estimated location is not confirmed.

11. An apparatus, comprising:
    an infrared (IR) camera mounted on a display;
    electroencephalographic (EEG) sensory probes;
    a processing resource; and
    a memory resource storing machine readable instructions to cause the processing resource to:
       track eye movements using the IR camera;

estimate an item to select on a display screen of the display based on the tracked eye movements;
detect EEG signals using the EEG sensory probes; and
confirm the estimated item to select based on the detected EEG signals.

12. The apparatus of claim 11, wherein the IR camera further comprises two IR cameras positioned in front of and facing toward eyes of a user of the apparatus.

13. The apparatus of claim 11, further comprising a camera positioned to detect gesture movement of a user.

14. The apparatus of claim 13, further comprising instructions executable by the processing resource to confirm the estimated item based on the detected gestures.

15. The apparatus of claim 11, wherein the IR camera is positioned a particular distance from eyes of a user to monitor a gaze of the eyes.

* * * * *